United States Patent [19]

Arai et al.

[11] Patent Number: 5,508,459
[45] Date of Patent: Apr. 16, 1996

[54] 2-METHYLDIALKOXYSILYL PROPIONIC ACID ESTER

[75] Inventors: Masatoshi Arai; Takafumi Sakamoto; Kei Miyoshi, all of Gunma, Japan

[73] Assignee: Shin-Etsu Chemical Co., Ltd., Tokyo, Japan

[21] Appl. No.: 404,574

[22] Filed: Mar. 15, 1995

[30] Foreign Application Priority Data

Mar. 16, 1994 [JP] Japan .................. 6-071658

[51] Int. Cl.⁶ ...................... C07F 7/08; C07F 7/18
[52] U.S. Cl. ............................................. 556/438
[58] Field of Search ............................... 556/438

[56] References Cited

U.S. PATENT DOCUMENTS

| | | | |
|---|---|---|---|
| 2,589,445 | 3/1952 | Sommer | 556/438 |
| 3,109,011 | 10/1963 | Pike et al. | 556/438 |
| 5,124,469 | 6/1992 | Takago et al. | 556/438 |
| 5,180,771 | 1/1993 | Arai et al. | 556/438 X |
| 5,286,892 | 2/1994 | Arai et al. | 556/438 |

*Primary Examiner*—Paul F. Shaver
*Attorney, Agent, or Firm*—Millen, White, Zelano & Branigan

[57] ABSTRACT

2-Methyldialkoxysilyl propionic acid esters defined by general chemical formula (1):

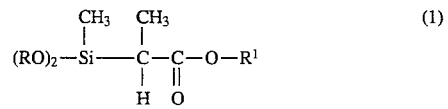

wherein R is an alkyl group with at most four carbon atoms, and $R^1$ is a monovalent, substituted or unsubstituted, hydrocarbon group with 1 to 12 carbon atoms, are novel compounds with good reactivity. These compounds are extremely useful as alkoxylation agents for the terminal groups of organopolysiloxanes, surface treatment agents for silica, stabilizers during storage and curing agents.

9 Claims, 4 Drawing Sheets

2-METHYLDIALKOXYSILYL PROPIONIC ACID ESTER

SUMMARY OF THE INVENTION

The invention relates to a novel organosilicone compound which is particularly useful as an alkoxylation agent.

Various types of alkoxy silanes are known as alkoxylation agents for the terminals of organopolysiloxanes such as α,ω-dihydroxypolydimethyl siloxane. However, conventionally known alkoxylation agents are not completely satisfactory in their reactivities. As a result, alkoxylation agents with further improved characteristics such as a good reactivity are desired.

Therefore, an object of the present invention is to provide novel organosilicone compounds which are useful, for example, as alkoxylation agents for the terminals of organopolysiloxanes.

Upon further study of the specification and appended claims, further objects and advantages of this invention will become apparent to those skilled in the art.

The present invention provides 2-methyldialkoxysilyl propionic acid ester compounds defined by the general chemical formula (1) below:

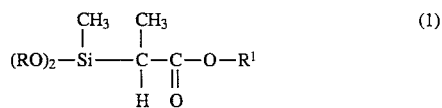
(1)

wherein R is an alkyl group with at most four carbon atoms, and $R^1$ is a substituted or unsubstituted monovalent hydrocarbon group with 1 to 12 carbon atoms.

Within formula (1), examples of the $C_1$-$C_{12}$ monovalent hydrocarbon group $R^1$ are: alkyl groups, alkenyl groups, aryl groups, and aralkyl groups, as well as such groups wherein at least a part of the hydrogen atoms are replaced by halogen atoms. Examples of substituted $R^1$ monovalent hydrocarbon groups are —$(CH_2)_2CF_3$, —$CF(CF_3)$—$(OCF_2CF(CF_3))_2F$, and —$(CH_2)_2CCl_3$. Among these groups, alkyl groups are most suitable in the present invention. The alkyl groups may be linear or branched, and desirable examples are: linear alkyl groups such as methyl, ethyl, propyl, butyl, hexyl, heptyl, octyl, nonyl and decyl; and branched alkyl groups such as a 2-ethylhexyl group. The most desirable $R^1$ groups in the present invention are ethyl and 2-ethylhexyl.

Further, R is a lower alkyl group with at most four carbon atoms. Thus, R can be methyl, ethyl, propyl, isopropyl, butyl, sec-butyl, or tert-butyl. Methyl is particularly suitable.

As is apparent from formula (1), the organosilicone compounds possess the structure of an α-silyl ester wherein the alkoxysilyl group is attached to the α-position carbon atom of the carbonyl group in the ester. In such an α-silyl ester, the bond between the silicon atom and the α-position carbon atom cleaves under relatively mild conditions. Therefore, the ester characteristically reacts with alcohols and silanols effectively. As a result, organosilicone compounds of the present invention, defined by formula (1) (i.e., 2-methyldialkoxysilyl propionic acid ester), are extremely useful as an alkoxylation agent for the terminals of organopolysiloxanes, such as a α,β-dihydroxypolydimethyl siloxane, which is industrially useful. Further, these compounds are also useful as surface treatment agents for silica and as stabilizers during storage for the de-alcoholized type of RTV.

Examples of industrial uses for alkoxylated organopolysiloxanes are in the fields of adhesion, sealing and coating, e.g., adhesion and sealing of electronic parts, flame resistant sealing and adhesion, high strength adhesion and seals, sealing and adhesion of plastic parts, etc.

In general, the alkoxylation reaction is conducted at room temperature to 120° C. and at a pressure of, e.g., 760 mmHg. The reaction can be performed without solvents or by using solvents such as aromatic solvents, e.g., toluene or xylene.

The organosilicone compounds of the present invention can be synthesized easily and at low cost through hydrosilylation (addition reaction of a hydrosilyl group to a carbon-carbon double bond) of, for example, an acrylic acid ester and an alkoxy silane having a SiH group (methyldialkoxy silane). This reaction is shown by equation (2) below:

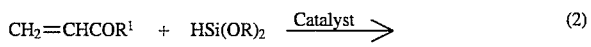

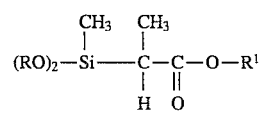

wherein R and $R^1$ are as described above.

This reaction is usually performed in the presence of an addition reaction catalyst. Examples of such catalysts are platinum metal type catalysts, for example, a platinum type, a palladium type, or a rhodium type. Among these catalysts, the platinum type catalysts are particularly suitable. Examples of platinum type catalysts are: platinum black or solid platinum carried by alumina, silica, etc.; chloroplatinic acid, and alcohol denatured chloroplatinic acid; complexes of chloroplatinic acid with olefins; and complexes of platinum with vinyl siloxanes. The amount of catalyst used is a catalytic amount. For example, 10 to 5000 ppm of platinum group metal equivalent can be used based on the total combined amount of acrylic acid ester and methyldialkoxy silane.

The reaction may be performed without using any solvents. However, appropriate solvents such as toluene or xylene may be used as necessary, so long as they do not have an appreciable adverse effect on the addition reaction.

Further, according to the reaction, small amounts of isomers expressed by the chemical formulae (3) and (4) below are also formed as by-products, in addition to the organic silicone compound of the present invention.

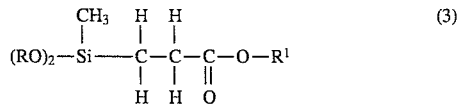
(3)

and

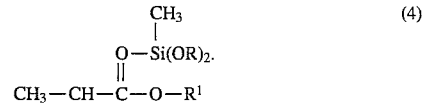
(4)

These by-products may be removed by processes such as distillation. However, their formation amount is very small. Further, these compounds are isomers of the organic silicone compounds of the present invention, expressed by formula (1). Therefore, these isomers will not have bad effects on the properties of the intended product. In reality, the reaction products may be utilized as an alkoxylation agent for the terminal groups, a surface treatment agent for silica, a stabilizer during storage, and a curing agent for condensation reactions, without removing these by-products.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding Japanese application No. 6-071658, filed Mar. 16, 1994, are hereby incorporated by reference.

EXAMPLES

Example 1

500.6 g (5 mol) of ethyl acrylate, 0.46 g of chloroplatinic acid ($H_2PtCl_6 \cdot 6H_2O$), and polymerization inhibitors, Irganox 1330 and BHT, were placed within a three liter capacity four-neck flask equipped with a dropping funnel, a condenser, a thermometer, and a stirrer, and the mixture was heated to 80° C. while stirring. Then 584.1 g (5.5 mol) of methyldimethoxy silane was added drop by drop while the mixture was stirred. At this time, the reaction was exothermic and the reaction temperature reached 80° to 90° C. This addition took an hour and half and the mixture continued to be heated to maintain the temperature at 80° to 90° C. for the next three hours.

After the reaction, distillation under reduced pressure resulted in a 773 g fraction with a boiling point of 82° to 83° C. at 18 mmHg (with 75% yield). According to the gas chromatography analysis and the analysis results below, this fraction was revealed to contain the following three compositions (a), (b) and (c) at the weight ratio of 92:2:6, respectively. Here the compositions (a), (b) and (c) are isomers.

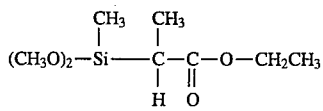

(a)

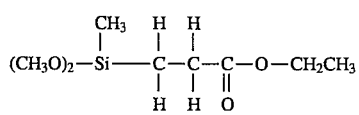

(b)

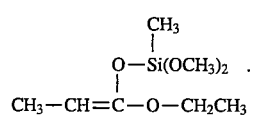

(c)

Analytical Results

Figure 1:
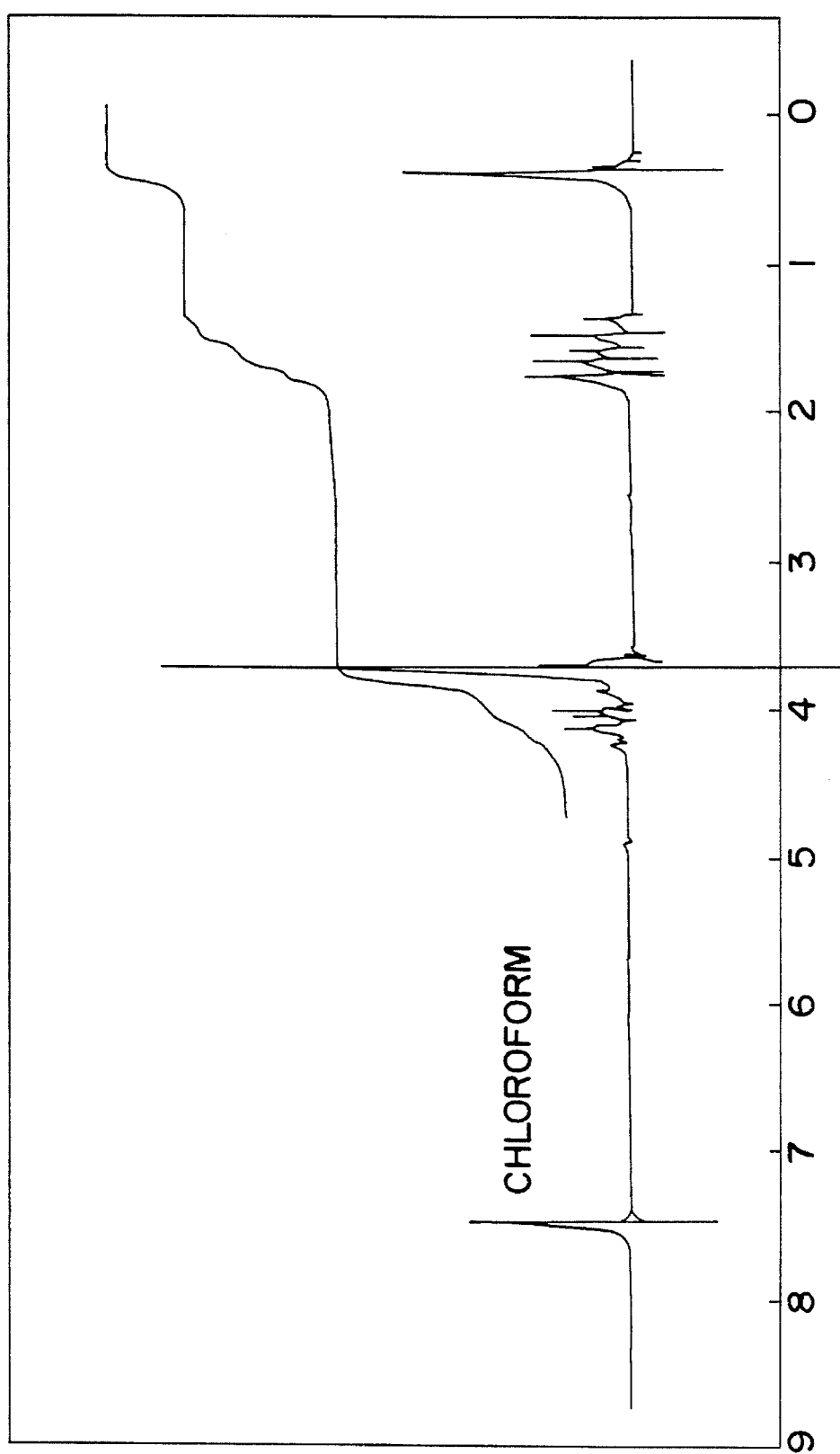
FIG. 1 is an NMR chart of the reaction product obtained in Example 1.

GS-MS analysis: m/e: 290 (molecular weight 290) NMR analysis: A chart is shown in FIG. 1.

| δ (ppm) | |
| --- | --- |
| 3.87 | (q, 2H) |
| 3.81 | (q, 1H) |
| 3.53 | (s, 6H) |
| 1.53 | (d, 3H) |
| 1.30 | (t, 3H) |
| 0.36 | (s, 3H) |

Figure 2:
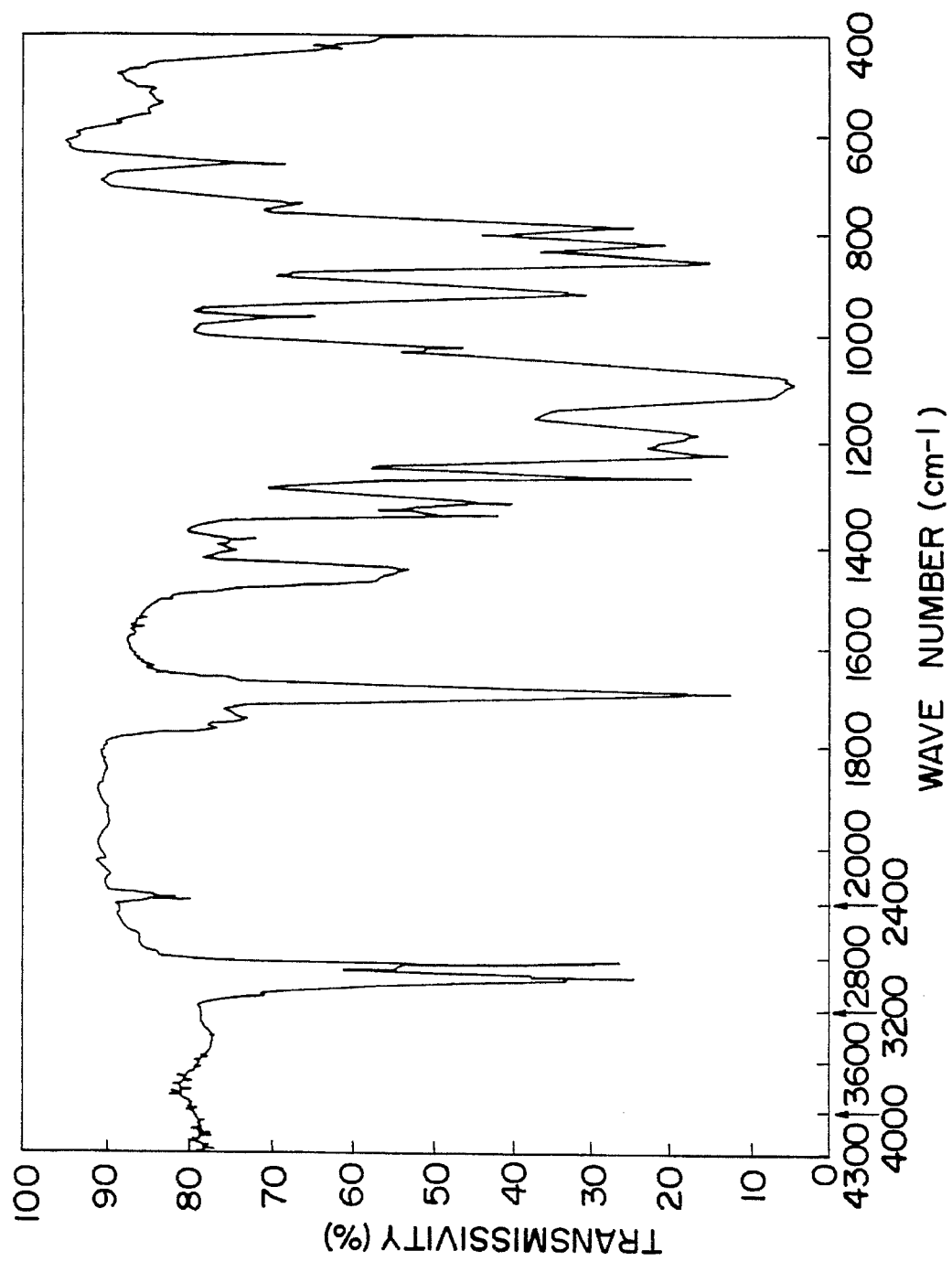
FIG. 2 is an IR chart of the reaction product obtained in Example 1.

IR analysis: A chart is shown in FIG. 2.

Example 2

921.4 g (5 mol) of 2-ethylhexyl acrylate, 0.46 g of chloroplatinic acid ($H_2PtCl_6 \cdot 6H_2O$), and polymerization inhibitors, Irganox 1330 and BHT, were placed within a three liter capacity four-neck flask equipped with a dropping funnel, a condenser, a thermometer, and a stirrer, and the mixture was heated to 80° C. while stirring. Then 584.1 g (5.5 mol) of methyldimethoxy silane was added drop by drop while the mixture was stirred. At this time, the reaction was exothermic and the reaction temperature reached 80° to 90° C. This addition took two hours and the mixture continued to be heated to maintain the temperature at 80° to 90° C. for the next three hours.

After the reaction, the distillation under reduced pressure resulted in a 942 g fraction with a boiling point of 138° to 142° C. at 5 mmHg (with 65% yield). According to the gas chromatography analysis and the analysis results below, this fraction was revealed to contain the following three compositions (a), (b) and (c) at the weight ratio of 90:2:8, respectively. Here the compositions (a), (b) and (c) are isomers.

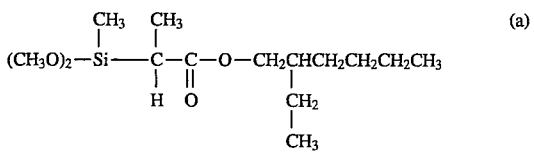

(a)

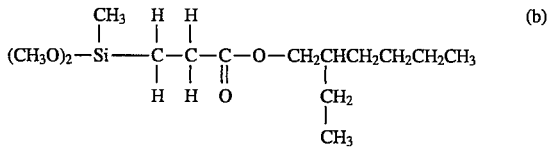

(b)

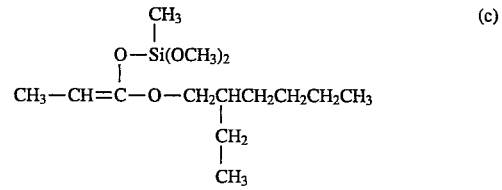

(c)

Analytical Results

Figure 3:
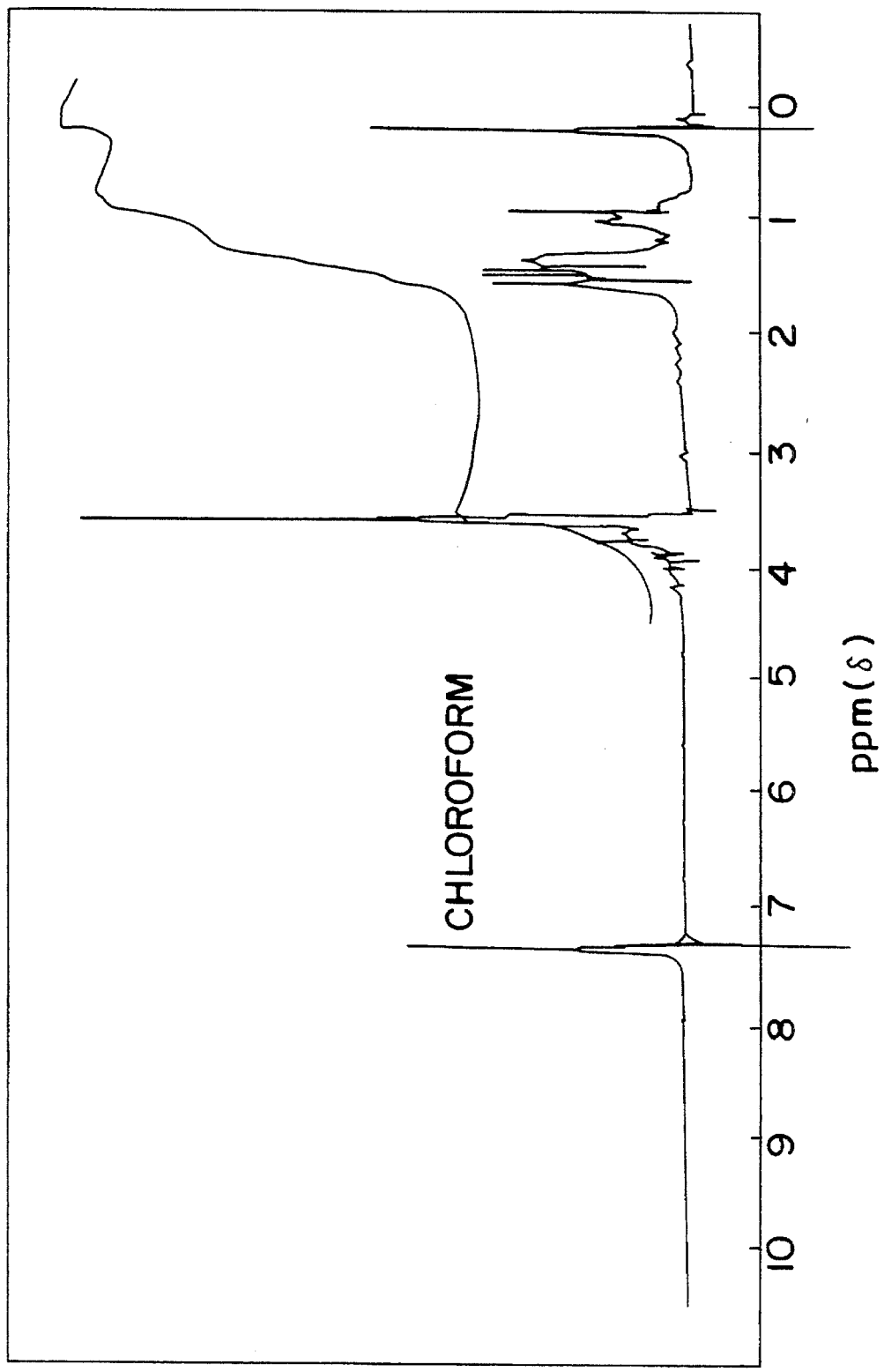
FIG. 3 is an NMR chart of the reaction product obtained in Example 2.

GS-MS analysis: m/e: 290 (molecular weight 290) NMR analysis: A chart is shown in FIG. 3.

| δ (ppm) | |
| --- | --- |
| 3.93 | (q, 2H) |
| 3.87 | (q, 1H) |
| 1.67–1.16 | (broad, 8H) |
| 1.52 | (d, 3H) |

| δ (ppm) | |
| --- | --- |
| 1.03 | (t, 6H) |
| 0.22 | (s, 3H) |

Figure 4:
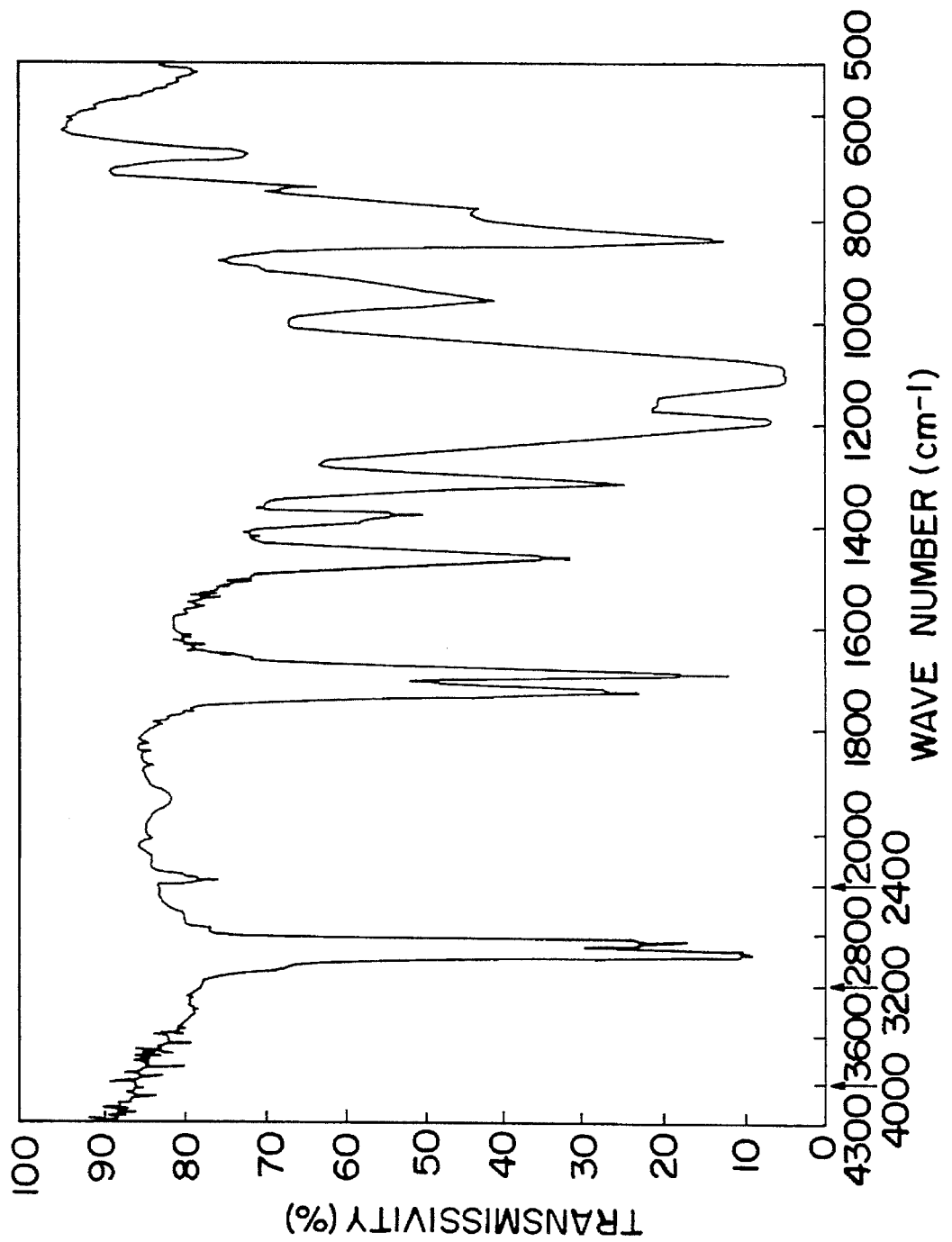
FIG. 4 is an IR charge of the reaction product obtained in Example 2.

IR analysis: A chart is shown in FIG. 4.

Example 3

2.90 g of 2-methyldimethoxysilyl propionic acid 2-ethylhexyl, which was obtained in Example 2, and 3.2 g of methanol were placed within a 50 ml capacity Erlenmeyer flask equipped with a magnetic stirrer and a stirrer. Further, 1.0 g of n-decane was added as an internal standard and the reaction between 2-methyldimethoxysilyl propionic acid 2-ethylhexyl and methanol was traced by gas chromatography. After 60 minutes, 2-methyldimethoxysilyl propionic acid 2-ethylhexyl completely reacted with methanol and produced methyltrimethoxy silane and propionic acid 2-ethylhexyl. Here methyltrimethoxy silane and propionic acid 2-ethylhexyl were identified by GC-MS analysis. This result indicates that the compound of the present invention easily reacts with alcohol at room temperature without catalysts.

The compound of the present invention, 2-methyldialkoxysilyl propionic acid ester, is a novel compound with a good reactivity; therefore, it is extremely useful as an alkoxylation agent for the terminal groups of organopolysiloxanes, a surface treatment agent for silica, a stabilizer during storage, and a curing agent.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for alkoxylating terminals of an organopolysiloxane using an alkoxylation agent, the improvement wherein said alkoxylation agent is a 2-methyldialkoxysilyl propionic acid ester of formula (1):

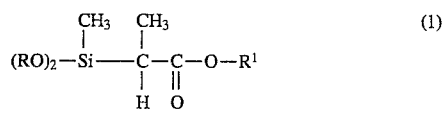

wherein

R is $C_1$–$C_4$-alkyl; and $R^1$ is a substituted or unsubstituted monovalent $C_1$–$C_{12}$-hydrocarbon group.

2. A process according to claim 1, wherein $R^1$ is alkyl, alkyl substituted by halogen atoms, alkenyl, alkenyl substituted by halogen atoms, aryl, aryl substituted by halogen atoms, aralkyl or aralkyl substituted by halogen atoms.

3. A process according to claim 1, wherein $R^1$ is a $C_1$–$C_{12}$-alkyl group.

4. A process according to claim 1, wherein $R^1$ is an alkyl group substituted by halogen atoms.

5. A process according to claim 1, wherein $R^1$ is alkenyl, aryl or aralkyl.

6. A process according to claim 1, wherein R is methyl.

7. A process according to claim 2, wherein R is methyl.

8. A process according to claim 3, wherein R is methyl.

9. A process according to claim 1, wherein R is methyl, ethyl, propyl, butyl, hexyl, heptyl, octyl, nonyl, decyl or 2-ethylhexyl.

\* \* \* \* \*